United States Patent
Yokosawa et al.

(10) Patent No.: US 11,052,051 B2
(45) Date of Patent: Jul. 6, 2021

(54) COATING COMPOSITION, DRUG-CONTAINING PARTICLE, SOLID PREPARATION AND METHOD FOR PREPARING DRUG-CONTAINING PARTICLE

(71) Applicant: Shin-Etsu Chemical Co., Ltd., Tokyo (JP)

(72) Inventors: Takuya Yokosawa, Niigata-ken (JP); Yuichi Nishiyama, Niigata-ken (JP); Naosuke Maruyama, Niigata-ken (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/151,205

(22) Filed: Jan. 9, 2014

(65) Prior Publication Data

US 2014/0199406 A1 Jul. 17, 2014

(30) Foreign Application Priority Data

Jan. 11, 2013 (JP) .............................. JP2013-003534

(51) Int. Cl.
*A61K 9/50* (2006.01)
*A61K 9/00* (2006.01)
*A61K 9/20* (2006.01)
*C09D 101/32* (2006.01)

(52) U.S. Cl.
CPC .......... *A61K 9/5047* (2013.01); *A61K 9/0056* (2013.01); *A61K 9/2081* (2013.01); *A61K 9/5042* (2013.01); *A61K 9/5078* (2013.01); *C09D 101/32* (2013.01)

(58) Field of Classification Search
CPC .. A61K 9/5047; A61K 9/5078; A61K 9/5042; A61K 9/0056; A61K 9/2081; C09D 101/32
See application file for complete search history.

(56) References Cited

U.S. PATENT DOCUMENTS

| | | |
|---|---|---|
| 2002/0031552 A1 | 3/2002 | McTeigue et al. |
| 2005/0281874 A1 | 12/2005 | Menjoge et al. |
| 2012/0161364 A1 | 6/2012 | Son et al. |
| 2012/0251588 A1 | 10/2012 | Fukasawa et al. |
| 2013/0224295 A1 | 8/2013 | Miyamoto et al. |
| 2013/0274348 A1 | 10/2013 | Sato et al. |

FOREIGN PATENT DOCUMENTS

| | | |
|---|---|---|
| EP | 0 466 566 A2 | 1/1992 |
| EP | 1 027 887 A2 | 8/2000 |
| EP | 1 166 777 A1 | 1/2002 |
| EP | 1 300 155 A1 | 4/2003 |
| EP | 1 749 518 A1 | 2/2007 |
| EP | 2 476 439 A1 | 7/2012 |
| EP | 2 510 923 A1 | 10/2012 |
| JP | 08-245423 A | 9/1996 |
| JP | 2002-087952 A | 3/2002 |
| JP | 2007-063263 A | 3/2007 |
| JP | 2008-214334 A | 9/2008 |
| JP | 2011-063627 A | 3/2011 |
| JP | 2012-214461 A | 11/2012 |
| WO | WO 2002/096392 A1 | 12/2002 |
| WO | WO 2004/041244 A2 | 5/2004 |
| WO | WO 2009/132208 A1 | 10/2009 |
| WO | WO 2011/030952 A1 | 3/2011 |
| WO | WO 2011/155686 A1 | 12/2011 |

OTHER PUBLICATIONS

Extended European Search Report from corresponding European Application No. 14150512.3, dated May 8, 2014.
Pharm Tech Japan, vol. 21(5), (2005) 163-169.
Office Action for Japanese Application No. 2013-003534 dated May 29, 2015.
Notice of Opposition for European Application No. 14150512.3 dated Nov. 23, 2017.
Opponent's Letter in Opposition for European Application No. 14150512.3 dated Nov. 16, 2017, 13 pages.
Opponent's Letter in Opposition for European Application No. 14150512.3 dated Jul. 12, 2018, 15 pages.
Pharmacoat (Brochure), Shin-Etsu Chemical Co., Ltd. (Oct. 2014) 12 pages.
Shin-Etsu AQOAT (Brochure), Shin-Etsu Chemical Co., Ltd. (Oct. 2005), 20 pages.
Japanese Pharmacopoeia, 16$^{th}$ Edition, Supplement 1 (2012) 2426-2428.
US Pharmacopoeia, NF 29 (2011) 1548-1550.
Japanese Pharmacopoeia, 16$^{th}$ Edition (2011) 1096-1098.
Japanese Pharmacopoeia, 16$^{th}$ Edition (2011) 940-942.
Klucel® hydroxypropylcellulose (Brochure) from Aqualon (Oct. 2001) 23 pages.

(Continued)

*Primary Examiner* — Hasan S Ahmed
(74) *Attorney, Agent, or Firm* — Rimon, P.C.

(57) ABSTRACT

Provided are a drug-containing particle capable of suppressing dissolution of a drug in the oral cavity to suppress an unpleasant taste thereof and having excellent dissolution of the drug in the digestive tract after passing through the oral cavity; a method for preparing the drug-containing particle; a coating composition used for preparing the drug-containing particle; and a solid preparation having the drug-containing particle. More specifically, provided are a coating composition having 100 parts by weight of a cellulose-based enteric base and 50 parts by weight or less of a water-soluble cellulose ether; a drug-containing particle having a drug-containing core and a coat portion obtained by coating the core with the coating composition; a solid preparation having the drug-containing particle; and a method for preparing a drug-containing particle having a step of coating the drug-containing core with the coating composition.

9 Claims, 1 Drawing Sheet

(56) References Cited

OTHER PUBLICATIONS

McGinity, J. W., *Aqueous Polymeric Coatings for Pharmaceutical Dosage Forms*, M. Dekker, New York (1989) 105-112.
Venkatesh, G. M. et al., *Development of Orally Disintegrating Tablets Comprising Controlled-Release Multiparticulate Beads*, Drug Development and Industrial Pharmacy, 38(12) (2012) 1428-1440.
Response to Summons to Attend Oral Hearing for Opposition Against European Application No. EP 2 754 438 dated Nov. 20, 2019 by letter from Fleischer Engels Patent, 9 pages.
Response to Communication dated Feb. 15, 2019 for European Application No. EP 2 754 438 by letter from Fleischer Engels Patent dated Mar. 12, 2019, 9 pages.

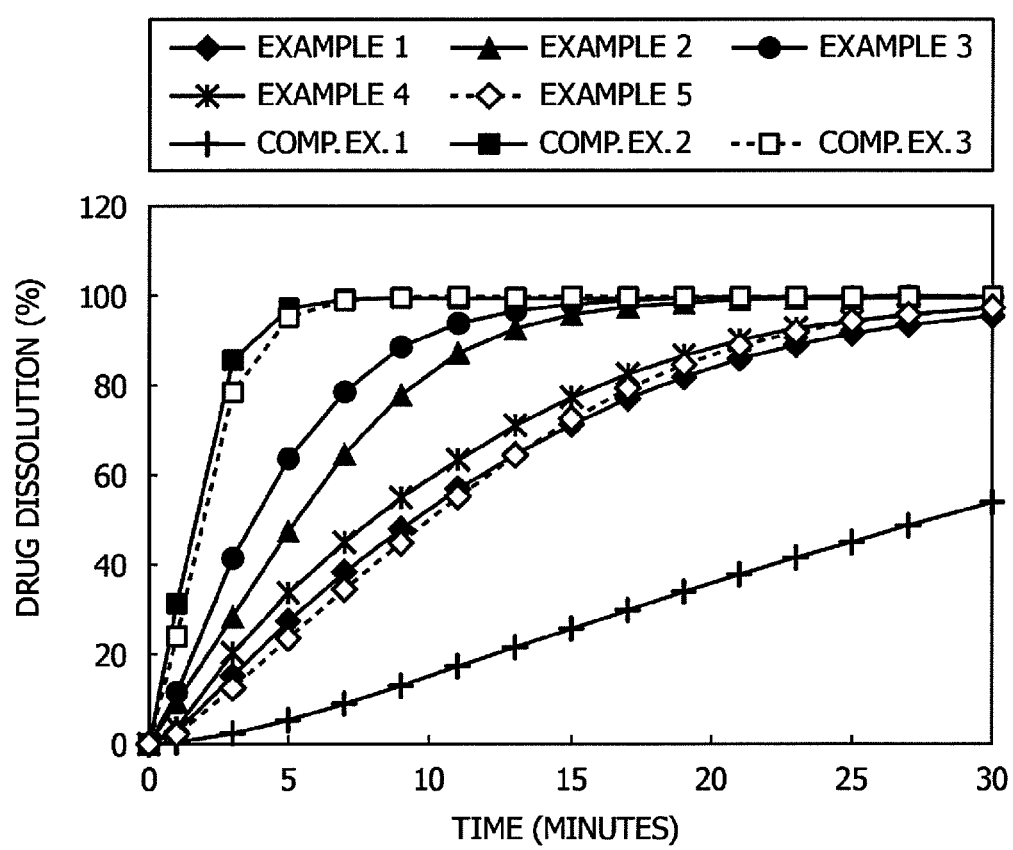

COATING COMPOSITION, DRUG-CONTAINING PARTICLE, SOLID PREPARATION AND METHOD FOR PREPARING DRUG-CONTAINING PARTICLE

FIELD

The present invention relates to a coating composition capable of masking an unpleasant taste of a drug in the oral cavity and releasing the drug smoothly after passing through the oral cavity; a drug-containing particle; a solid preparation comprising the drug-containing particle; and a method for preparing the drug-containing particle.

BACKGROUND

In recent years, there has been a demand for the development of orally disintegrating tablets that can be taken easily without water by elderly or pediatric patients having low swallowing ability. When a drug contained in orally disintegrating tablets has an unpleasant taste such as bitterness, since the drug sometimes starts dissolution in the oral cavity, its administration is made difficult. For suppressing dissolution of a drug in the oral cavity, a method of coating the drug with a water-insoluble coating base can be considered. However, this method has the problem that a dissolution amount of the drug in the digestive organ is also suppressed, and the drug is prevented from exerting its sufficient effect.

Examples of particles capable of suppressing an unpleasant taste of a drug in the oral cavity and having excellent dissolution in the digestive tract include an amlodipine-containing particle coated with a composition comprising a carrier for forming a continuous layer (JP 2007-63263A), a drug-containing particle having a drug-containing composition coated with an enteric polymer, a disintegrant and an anticoagulator, where the drug has an unpleasant taste (JP 2008-214334A); and a drug-containing particle comprising a core containing a drug having a bitter taste; and a masking film for coating the core therewith (JP 2011-63627A).

SUMMARY

Although JP 2007-63263A describes that the carrier for forming a continuous layer comprises a water-soluble polymer, a water-insoluble polymer, a gastric polymer, an enteric polymer and a thermoplastic substance, JP 2007-63263A is silent about a mixing ratio of them. Thus, the dissolution of the drug cannot be controlled easily. The coating composition described in JP 2008-214334A contains the disintegrant so that the drug-containing particle is inferior in stability. The method as described in JP 2011-63627A in which the core is coated with an aqueous dispersion of an acrylic polymer may have difficulty in controlling dissolution because of inferiority in uniformity of the film. Thus, it is difficult in the conventional art to satisfy both sufficient suppression of an unpleasant taste in the oral cavity and dissolution in the digestive tract.

In view of the foregoing, the present invention has been made. An object of the invention is to provide a drug-containing particle capable of suppressing dissolution of the drug in the oral cavity so as to suppress an unpleasant taste of the drug and having excellent dissolution of the drug in the digestive tract after passing through the oral cavity; a method for preparing the drug-containing particle; a coating composition to be used for the preparation of the drug-containing particle; and a solid preparation comprising the drug-containing particle.

With a view to achieving the above-mentioned object, the present inventors have carried out an extensive investigation. As a result, the above-mentioned object is achieved by coating a drug-containing core with a coating composition comprising a cellulose-based enteric base and a water-soluble cellulose ether, leading to the completion of the invention.

According to the present invention, there is provided a coating composition comprising 100 parts by weight of a cellulose-based enteric base and 50 parts by weight or less of a water-soluble cellulose ether. There is also provided a drug-containing particle comprising a drug-containing core and a coat portion on the drug-containing core obtained by coating the dug-containing core with the coating composition. There is further provided a solid preparation comprising the drug-containing particle. There is still further provided a method for preparing a drug-containing particle comprising a step of coating a drug-containing core with the coating composition.

According to the present invention, a dug-containing particle capable of suppressing dissolution of a drug contained therein in the oral cavity so as to suppress an unpleasant taste of the drug and having excellent dissolution of the drug in the digestive tract after passing through the oral cavity can be provided by coating the drug-containing core with a coating composition comprising a cellulose-based enteric base and a water-soluble cellulose ether. An oral solid preparation comprising the drug-containing particle can be also provided.

BRIEF DESCRIPTION OF THE DRAWING

FIG. 1 shows the results of a dissolution test of drug-containing particles and orally disintegrating tablets obtained in Examples 1 to 5 and Comparative Examples 1 to 3.

DETAILED DESCRIPTION

The coating composition comprises a cellulose-based enteric base and a water-soluble cellulose ether.

Examples of the cellulose-based enteric base include hydroxypropylmethyl cellulose acetate succinate (hereinafter also referred to as "HPMCAS), hydroxypropylmethyl cellulose phthalate, and carboxyacetyl cellulose. Of these, HPMCAS is particularly preferred because it is uniformly soluble in a solvent easily. The cellulose-based enteric base may be used singly or as a mixture of two or more kinds thereof.

The contents of the substituents of HPMCAS are not particularly limited. The content of a methoxy group is preferably from 12 to 28% by weight, more preferably from 20 to 26% by weight; the content of a hydroxypropoxy group is preferably from 4 to 23% by weight, more preferably from 5 to 10% by weight; the content of an acetyl group is preferably from 2 to 16% by weight, more preferably from 5 to 14% by weight; and the content of a succinoyl group is from 2 to 20% by weight, more preferably from 4 to 18% by weight. The degree of substitution for such substituents can be determined according to the method described in the Japanese Pharmacopoeia, Sixteenth Edition, Supplement I.

The viscosity of HPMCAS is not particularly limited. The viscosity at 20° C. of an aqueous 2% by weight HPMCAS solution is preferably from 1 to 50 mPa·s, more preferably from 1 to 25 mPa·s, particularly preferably from 1 to 15 mPa·s. When the viscosity is less than 1 mPa·s, strength of the resulting film may not be kept sufficient owing to extreme reduction in the degree of polymerization of the cellulose-based enteric base. When the viscosity is more than 50 mPa·s, the concentration of the aqueous coating solution has to be lowered, which may not be practical. The viscosity can be determined according to the method described in the Japanese Pharmacopoeia, Sixteenth Edition and the Japanese Pharmacopoeia, Sixteenth Edition, Supplement I.

The water-soluble cellulose ether is a nonionic polymer obtained by etherifying a part of the hydroxyl groups of the glucose ring of cellulose. Examples thereof include alkyl celluloses such as methyl cellulose (hereinafter also referred to as "MC"); hydroxyalkyl celluloses such as hydroxypropyl cellulose; and hydroxyalkylalkyl celluloses such as hydroxypropylmethyl cellulose (also called "hypromellose" in the Japanese Pharmacopoeia, hereinafter also referred to as "HPMC"). The water-soluble cellulose ether may be used singly or in combination of two or more kinds thereof.

The degree of substitution of the water-soluble cellulose ether is not particularly limited, and hydroxypropylmethyl cellulose, methyl cellulose, hydroxypropyl cellulose and the like specified in the Japanese Pharmacopoeia can be used. For example, with regard to hydroxypropylmethyl cellulose, the degree of methoxy substitution is preferably from 16.5 to 30.0% by weight, more preferably from 19.0 to 30.0% by weight, particularly preferably from 28.0 to 30.0% by weight; the degree of hydroxypropoxy substitution is preferably from 4.0 to 32.0% by weight, more preferably from 4.0 to 12.0% by weight, particularly preferably from 7.0 to 12.0% by weight. With regard to methyl cellulose, the degree of methoxy substitution is preferably from 26.0 to 33.0% by weight, more preferably from 28.0 to 31.0% by weight. The degree of substitution for these groups can be determined according to the method for measuring the degree of substitution of hydroxypropylmethyl cellulose, methyl cellulose and hydroxypropyl cellulose described in the Japanese Pharmacopoeia, Sixteenth Edition.

The viscosity of the water-soluble cellulose ether is not particularly limited. The viscosity at 20° C. of an aqueous 2% by weight solution of the water-soluble cellulose ether is preferably from 2 to 50 mPa·s, more preferably from 2 to 25 mPa·s, particularly preferably from 2 to 15 mPa·s. When the viscosity is less than 2 mPa·s, strength of the resulting film may not be kept sufficient owing to extreme reduction in the degree of polymerization of the water-soluble cellulose. When the viscosity is more than 50 mPa·s, the concentration of the aqueous coating solution has to be lowered, which may not be practical. The viscosity can be determined according to the viscosity measurement method described in the Japanese Pharmacopoeia, Sixteenth Edition.

With regard to a ratio of the water-soluble cellulose ether to the cellulose-based enteric base in the coating composition, the water-soluble cellulose ether is in an amount of 50 parts by weight or less, preferably from 10 to 45 parts by weight, more preferably from 10 to 25 parts by weight, based on 100 parts by weight of the cellulose-based enteric base. The coating composition comprising the cellulose-based enteric base in the absence of the water-soluble cellulose ether can reduce the unpleasant taste of a drug, but is inferior in subsequent dissolution of the drug in the digestive tract. On the other hand, the coating composition comprising the water-soluble cellulose ether in an amount of more than 50 parts by weight cannot reduce the unpleasant taste because dissolution of the drug occurs in the oral cavity.

The coating composition may optionally comprise a various kind of additive conventionally usable in this field such as a lubricant, the other coating base, a plasticizer, a surfactant, a colorant, a pigment, a sweetener and an antifoaming agent in a conventionally used amount.

Examples of the optional lubricant include talc, magnesium stearate, calcium stearate, colloidal silica and stearic acid. The content of the lubricant is not particularly limited insofar as it does not interfere with the advantageous effect of the invention. The content of the lubricant is preferably 200 parts by weight or less, more preferably 100 parts by weight or less, based on 100 parts by weight of the cellulose-based enteric base. Of the above-mentioned ones, talc is preferred from the viewpoint of preventing adhesion between particles during coating.

Examples of the other coating base as an optional additive include water-soluble vinyl derivatives such as polyvinylpyrrolidone and polyvinyl alcohol; water-insoluble cellulose ethers such as ethyl cellulose; and acrylic acid-based copolymers such as methacrylic acid copolymer LD and a copolymer dispersion of ethyl acrylate and methyl methacrylate. The content of the other coating base is not particularly limited insofar as it does not interfere with the advantageous effect of the invention. The content of the other coating base is preferably 100 parts by weight or less, more preferably 50 parts by weight or less, based on 100 parts by weight of the cellulose-based enteric base.

Examples of the optional plasticizer include glycerin, polyethylene glycols, propylene glycol, triethyl citrate, glycerin fatty acid esters, triacetin, and dibutyl phthalate. The content of the plasticizer is not particularly limited insofar as it does not interfere with the advantageous effect of the invention. The amount of the plasticizer is preferably 100 parts by weight or less, more preferably 50 parts by weight or less, based on 100 parts by weight of the cellulose-based enteric base.

Next, the drug-containing particle will be described.

The drug-containing particle comprises a drug-containing core and a coat portion on the drug-containing core obtained by coating the drug-containing core with the coating composition.

Any drug can be used for the drug-containing particle insofar as the drug is orally administrable. The invention is particularly effective on the drug having an unpleasant taste such as bitterness or astringency. Examples of the drug having such an unpleasant taste include acetaminophen, aspirin, ibuprofen, ethenzamide, phenacetin, mefenamic acid, antipyrine, phenylbutazone, sulpyrine, diclofenac sodium, ketoprofen, naproxen, loxoprofen sodium, etodolac, epirizole, tiaramide hydrochloride, indomethacin, pentazocine, acetylcholine chloride, alimemazine tartrate, cyproheptadine hydrochloride, diphenhydramine hydrochloride, chlorpheniramine maleate, codeine phosphate, dihydrocodeine phosphate, dextromethorphan hydrobromide, pentoxyverine citrate, theophylline, aminophylline, ephedrine hydrochloride, epinephrine hydrochloride, salbutamol sulfate, trimetoquinol hydrochloride, procaterol hydrochloride, methylephedrine hydrochloride, phenylpropanolamine hydrochloride, guaifenesin, tranexamic acid, anhydrous caffeine, caffeine, choline salicylate and sodium salicylate. The drug may be used singly or in combination of two or more kinds thereof.

The drug-containing core may be a drug substance; a granulated particle obtained by wet granulation, dry granulation or the like; or a layered particle obtained by coating a core such as crystalline cellulose, mannitol or lactose with a drug or layering the drug onto the core. When the drug-containing core is prepared by granulation or layering, a various additive conventionally used in this field such as an excipient, a binder and a disintegrant may be incorporated.

An amount of the coating composition to be applied onto the surface of the drug-containing core may vary depending on the shape or size of the core, the properties of the drug or additive contained in the core, or the like. In general, the coating amount, in terms of a total amount of the cellulose-based enteric base and the water-soluble cellulose ether, may be preferably from 1 to 500 parts by weight, more preferably from 5 to 100 parts by weight, particularly preferably from 10 to 50 parts by weight, based on 100 parts by weight of the drug-containing core. When the coating amount is below the above-mentioned range, sufficient suppression of an unpleasant taste may not be achieved. When the coating amount exceeds the above-mentioned range, it takes long hours for preparation so that it may not be practical.

The coat portion is not limited insofar as it comprises the coating composition. The coat portion (coat layer) may consist of the coating composition or may comprise an undercoat of another coating base material under the coat of the coating composition. Another coating base material can be a various coating base conventionally usable in this field such as HPMC. The coat portion may be in any form, for example, in layered form or in film form.

The average particle size of the drug-containing particle obtained by coating the drug-containing core with the coating composition is preferably 300 μm or less, more preferably 250 μm or less in order to prevent the particle from causing unpleasant roughness in the oral cavity.

It is noted that the average particle size is a volume-based particle size and measured by using a powder particle size measurement method with laser diffraction. For example, it can be measured, for example, using HELOS & RODOS (product of Japan Laser Corporation).

Next, a method for preparing the drug-containing particle will be described.

The drug-containing particle can be prepared by coating the drug-containing core with the coating composition by using a conventionally known coating apparatus.

Examples of the coating method include a method of dissolving or dispersing the coating composition in a solvent to prepare a solution of the coating composition and then applying the resulting solution to the drug-containing core.

As the solvent for dissolving the coating composition therein, a solvent capable of dissolving therein both the cellulose-based enteric base and the water-soluble cellulose ether is preferred. It is preferred to select, for example, an aqueous 0.01 to 1.0% by weight ammonia solution, a mixed solution of water and ethanol (a weight ratio of water to ethanol is preferably from 90:10 to 10:90), or a mixed solution of water and methanol (a weight ratio of water to methanol is preferably from 90:10 to 10:90). The aqueous 0.01 to 1.0% by weight ammonia solution is particularly preferred because no organic solvent is contained.

The preparation method may further comprise a step of undercoating the drug-containing core with a various coating base conventionally usable in this field such as HPMC so that the undercoat is formed between the drug-containing core and the film of the coating composition. As a result, a plurality of films are formed.

The coating apparatus is not particularly limited. For example, a pan coating apparatus, a fluidized bed granulator, or a tumbling fluidized bed coating apparatus may be used.

Coating the core containing the drug having an unpleasant taste with the coating composition makes it possible to suppress dissolution of the drug in the oral cavity and thereby suppress the unpleasant taste of the drug. When the drug-containing particle of the invention is evaluated by the Syringe Erection/Inversion Test (refer to Pharm Tech Japan, Vol. 21(5), 163-169, 2005), which is a simple dissolution test for reproducing the dissolution of a drug in the oral cavity, the drug dissolution after 30 seconds is preferably 10% or less, more preferably 5% or less.

The drug-containing particle is excellent in drug dissolution after it passes through the oral cavity. When the Dissolution Test (at 37° C., paddle method, 100 revolutions per minute, solvent: 900 ml of purified water) described in the Japanese Pharmacopoeia, Sixteenth Edition is conducted, the drug dissolution after 30 minutes is preferably 80% or more, more preferably 90% or more.

Next, a solid preparation comprising the drug-containing particle will be described.

Examples of the solid preparation include tablets, granules, fine granules and capsules. They also include orally disintegrating tablets. The solid preparation may comprise, in addition to the drug-containing particle, a various additive conventionally usable in this field such as an excipient, a binder, a disintegrant, a lubricant, an anticoagulant, and a solubilizing agent for a pharmaceutical compound.

Examples of the excipient include saccharides such as sucrose, lactose and glucose; sugar alcohols such as mannitol, sorbitol and erythritol; starches; crystalline cellulose; calcium phosphate; and calcium sulfate.

Examples of the binder include polyvinyl alcohol, polyacrylic acid, polymethacrylic acid, polyvinylpyrrolidone, glucose, sucrose, lactose, maltose, dextrin, sorbitol, mannitol, hydroxyethyl cellulose, hydroxypropylmethyl cellulose, hydroxypropyl cellulose, macrogols, gum arabic, gelatin, agar and starches.

Examples of the disintegrant include low-substituted hydroxypropyl cellulose, carmellose or salt thereof, croscarmellose sodium, carboxymethyl starch sodium, crospolyvinylpyrrolidone, crystalline cellulose, and crystalline cellulose-carmellose sodium.

Examples of the lubricant and the anticoagulant include talc, magnesium stearate, calcium stearate, colloidal silica, stearic acid, waxes, hydrogenated oils, polyethylene glycols and sodium benzoate.

Examples of the solubilizing agent for a pharmaceutical compound include organic acids such as fumaric acid, succinic acid, malic acid and adipic acid.

The solid preparation can be prepared in a conventional manner under conventional conditions.

EXAMPLES

Although the invention will hereinafter be described more specifically by Examples, it should not be construed that the invention is limited by these Examples. Many modifications can be achieved by those skilled in the art within the technical concept of the invention.

Example 1

Preparation of Core

A core was prepared in the following manner under the following layering conditions.

A drug layering solution was prepared by dissolving 324 g of acetaminophen (product of Yamamoto Corporation) and 36 g of hydroxypropylmethyl cellulose (degree of methoxy substitution: 29% by weight, degree of hydroxypropoxy substitution: 10% by weight, viscosity at 20° C. of an aqueous 2% by weight solution: 3 mPa·s) in a solution of 1008 g ethanol and 432 g purified water. Next, 600 g of crystalline cellulose spherical granules ("CELPHERE CP-102", product of Asahi Kasei Chemicals) were placed in a fluidized bed granulator ("MP-01", SPC, product of Powrex Corp). The layering solution was then sprayed in an amount of up to 50 parts by weight of acetaminophen based on 100 parts by weight of the crystalline cellulose spherical granules under the following conditions to obtain drug-containing cores. The drug-containing cores had an average particle size of about 200 μm.

Layering Conditions
Temperature of air intake: from 50 to 60° C.
Temperature of exhaust air: from 24 to 31° C.
Air flow rate: from 0.7 to 1.0 m$^3$/min
Spray rate: from 15 to 20 g/min
Spray air pressure: from 0.2 to 0.3 MPa Preparation of Drug-Containing Particles Next, a coating solution was prepared by dissolving 5.4 parts by weight of hydroxypropylmethyl cellulose acetate succinate (HPMCAS, methoxy group: 23% by weight, hydroxypropoxy group: 7% by weight, acetyl group: 9% by weight, succinoyl group: 11% by weight) as the cellulose-based enteric base and 0.6 part by weight of methyl cellulose (MC, methoxy group: 30% by weight, viscosity at 20° C. of an aqueous 2% by weight solution: 4 mPa·s) (a ratio of MC to HPMCAS: 11% by weight) in an aqueous 0.11% by weight ammonia solution (0.10 parts by weight of ammonia in 92.1 parts by weight of purified water) and adding 1.8 parts by weight of talc to the resulting solution.

Next, 500 g of the drug-containing cores prepared above was placed in a fluidized bed granulator ("MP-01", SPC, product of Powrex Corp). The coating solution was sprayed in an amount of up to 30 parts by weight of a total weight of the cellulose-based enteric base and water-soluble cellulose ether based on 100 parts by weight of the drug-containing cores under the following conditions to obtain drug-containing particles. The drug-containing particles had an average particle size of about 230 μm.

Coating Conditions:
Temperature of air intake: from 60 to 70° C.
Temperature of exhaust air: from 29 to 36° C.
Air flow rate: from 0.7 to 1.0 m$^3$/min
Spray rate: from 10 to 15 g/min
Spray air pressure: from 0.2 to 0.3 MPa Example 2

A coating solution was prepared in the same manner as in Example 1 except that 4.8 parts by weight of HPMCAS, 1.2 parts by weight of MC (a ratio of MC to HPMCAS: 25% by weight), an aqueous 0.098% by weight ammonia solution of ammonia (0.09 part by weight of ammonia in 92.11 parts by weight of purified water) and 1.8 parts by weight of talc were used. Then drug-containing particles were obtained in the same manner as in Example 1.

Example 3

A coating solution was prepared in the same manner as in Example 1 except that 4.2 parts by weight of HPMCAS, 1.8 parts by weight of MC (a ratio of MC to HPMCAS: 43% by weight), an aqueous 0.087% by weight ammonia solution (0.08 part by weight of ammonia in 92.12 parts by weight of purified water) and 1.8 parts by weight of talc were used. Then drug-containing particles were obtained in the same manner as in Example 1.

Comparative Example 1

A coating solution was prepared in the same manner as in Example 1 except that 6.0 parts by weight of HPMCAS, none of MC, an aqueous 0.12% by weight ammonia solution (0.11 part by weight of ammonia in 92.09 parts by weight of purified water) and 1.8 parts by weight of talc were used. Then drug-containing particles were obtained in the same manner as in Example 1.

Comparative Example 2

A coating solution was prepared in the same manner as in Example 1 except that 3.9 parts by weight of HPMCAS, 2.1 parts by weight of MC (a ratio of MC to HPMCAS: 54% by weight), an aqueous 0.076% by weight ammonia solution (0.07 part by weight of ammonia in 92.13 parts by weight of purified water) and 1.8 parts by weight of talc were used. Then drug-containing particles were obtained in the same manner as in Example 1.

Example 4

A coating solution was prepared in the same manner as in Example 1 except that 5.4 parts by weight of HPMCAS, 0.6 part by weight of hydroxypropylmethyl cellulose (HPMC, methoxy group: 29% by weight, hydroxypropoxy group: 10% by weight, viscosity at 20° C. of an aqueous 2% by weight solution: 3 mPa·s) as the water-soluble cellulose ether (a ratio of HPMC to HPMCAS: 11% by weight), an aqueous 0.11% by weight ammonia solution (0.10 part by weight of ammonia in 92.1 parts by weight of purified water) and 1.8 parts by weight of talc were used. Then drug-containing particles were obtained in the same manner as in Example 1.

Example 5

The 285 g of D-mannitol was placed in a fluidized bed granulator. Then 214 g of an aqueous 7% by weight dispersion of low-substituted hydroxypropyl cellulose (degree of hydroxypropoxy substitution: 14% by weight, average particle size: 35 μm) was sprayed thereto at the temperature of air intake of 60° C., the temperature of exhaust air of from 27 to 30° C., an air flow rate of 50 m$^3$/hr, a spray rate of 12 g/min and a spray air pressure of 150 kPa to obtain granulated mannitol. The 80 parts by weight of the resulting granulated mannitol and 20 parts by weight of the drug-containing particles obtained in Example 1 were mixed, and then 0.5 part by weight of magnesium stearate as a lubricant was added thereto and mixed. The resulting mixture was tableted into tablets, each having a diameter of 8 mm, a radius of curvature of 12 mm and a tablet weight of 200 mg, by using a rotary tableting machine (product of KIKUSUI SEISAKUSHO LTD.) under a tableting pressure of 7.5 kN to obtain orally disintegrating tablets comprising the drug-containing particles.

Comparative Example 3

Orally disintegrating tablets were prepared in the same manner as in Example 5 except that the drug-containing particles of Comparative Example 2 were used.
<Evaluation of Dissolution Property>
The dissolution property of the drug-containing particles and the orally disintegrating tablets comprising the drug-containing particles obtained in Examples 1 to 5 and Comparative Examples 1 to 3 was evaluated in accordance with the Dissolution Test (37° C., paddle method, 100 revolutions per minute, solvent: 900 mL of purified water) described in the Japanese Pharmacopoeia, Sixteenth Edition. The dissolution behavior of the particles and tablets obtained in Examples 1 to 5 and Comparative Examples 1 to 3 is shown in FIG. 1. In addition, the drug dissolution after 30 minutes from the start of the Dissolution Test is shown in Table 1 with respect to the particles obtained in Examples 1 to 4 and Comparative Examples 1 and 2.

It is evident in FIG. 1 and Table 1 that the drug-containing particles and the orally disintegrating tablets comprising the drug-containing particles according to the invention show the drug dissolution of 90% or more after 30 minutes from the start of the test, while the drug-containing particles of Comparative Example 1 show the dissolution of as low as about 60%.
<Evaluation of Masking Property>
The Syringe Erection/Inversion Test was conducted in order to evaluate the masking property of the drug-containing particles obtained in Examples 1 to 4 and Comparative Examples 1 and 2. In other words, the drug-containing particles were entered into a 10-mL syringe so that 300 mg of acetaminophen was enclosed. Then 10 mL of purified water was added thereto. The resulting syringe was erected and inverted repeatedly once every three seconds for 30 seconds. Then, the quantity of acetaminophen in the solution which had passed through a filter was measured using an ultraviolet absorption meter ("UV-1700", product of Shimadzu Corporation) at a measuring wavelength of 244 nm. The dissolution after 30 seconds is shown in Table 1 with respect to the particles obtained in Examples 1 to 4 and Comparative Examples 1 and 2.

The particles obtained in Examples 1 to 4 show the dissolution of 10% or less as of 30 seconds, indicating that bitterness can be suppressed substantially. On the other hand, the particles obtained in Comparative Example 2 show the drug dissolution of about 20%, indicating that bitterness cannot be suppressed.
<Evaluation of Masking Property of Orally Disintegrating Tablets>

Each of the orally disintegrating tablets obtained in Example 5 and Comparative Example 3 was administered to 10 healthy adults and whether the adults felt bitterness in their oral cavity or not was tested. All of the 10 adults felt strong bitterness from the orally disintegrating tablets obtained in Comparative Example 3, while none of the 10 adults felt bitterness from the orally disintegrating tablets obtained in Example 5.

TABLE 1

| | enteric base (A) | Water-soluble cellulose ether (B) | | | aqueous ammonia solution | | | Dissolution Test | Syringe Erection/Inversion Test |
| | | | | | | | | dissolution | dissolution |
| | HPMCAS (wt. part) | MC (wt. part) | HPMC (wt. part) | B/A (%) | ammonia (wt. part) | purified water (wt. part) | talc (wt. part) | after 30 minutes (%) | after 30 seconds (%) |
| --- | --- | --- | --- | --- | --- | --- | --- | --- | --- |
| Example 1 | 5.4 | 0.6 | — | 11 | 0.10 | 92.10 | 1.8 | 96 | 3 |
| Example 2 | 4.8 | 1.2 | — | 25 | 0.09 | 92.11 | 1.8 | 100 | 5 |
| Example 3 | 4.2 | 1.8 | — | 43 | 0.08 | 92.12 | 1.8 | 100 | 8 |
| Example 4 | 5.4 | — | 0.6 | 11 | 0.10 | 92.10 | 1.8 | 97 | 3 |
| Comp. Ex. 1 | 6.0 | — | — | 0 | 0.11 | 92.09 | 1.8 | 54 | 0 |
| Comp. Ex. 2 | 3.9 | 2.1 | — | 54 | 0.07 | 92.13 | 1.8 | 100 | 18 |

The invention claimed is:

1. A coating composition comprising: 100 parts by weight of a cellulose-based enteric base and 10 to 45 parts by weight of a water-soluble cellulose ether, and 0 parts by weight of a water-insoluble cellulose ether excluding the cellulose-based enteric base, wherein the cellulose-based enteric base is hydroxypropylmethyl cellulose acetate succinate or hydroxypropylmethyl cellulose phthalate, and the water-soluble cellulose ether is methyl cellulose or hydroxypropylmethyl cellulose.

2. The coating composition according to claim 1, wherein the cellulose-based enteric base is hydroxypropylmethyl cellulose acetate succinate.

3. A drug-containing particle comprising:
a drug-containing core and
a coat portion on the drug-containing core obtained by coating the drug-containing core with the coating composition as claimed in claim 1.

4. The drug-containing particle according to claim 3, wherein the drug-containing particle has an average particle size of 300 μm or less.

5. A solid preparation comprising the drug-containing particle as claimed in claim 3.

6. The solid preparation according to claim 5, wherein the solid preparation is an orally disintegrating tablet.

7. A method for preparing a drug-containing particle, comprising a step of coating a drug-containing core with the coating composition as claimed in claim 1.

8. The method for preparing a drug-containing particle according to claim 7, wherein the step of coating comprises application of a solution obtained by dissolving the coating composition in a solvent to the drug-containing core.

9. The method for preparing a drug-containing particle according to claim 8, wherein the solvent is an aqueous solution of ammonia.

\* \* \* \* \*